United States Patent [19]

Eisenbarth et al.

[11] Patent Number: 5,422,339

[45] Date of Patent: Jun. 6, 1995

[54] PEPTIDES HAVING INSULIN AUTOANTIBODY BUT NOT INSULIN RECEPTOR BINDING CAPACITY

[75] Inventors: George S. Eisenbarth, Wellesley, Mass.; Luis Castano, Asturias, Spain; Steven E. Shoelson, Natick, Mass.

[73] Assignee: Joslin Diabetes Center, Inc., Boston, Mass.

[21] Appl. No.: 212,696

[22] Filed: Mar. 14, 1994

Related U.S. Application Data

[63] Continuation of Ser. No. 671,455, Mar. 19, 1991, abandoned.

[51] Int. Cl.$^6$ .................... A61K 38/28; A61K 38/00; C07K 14/00
[52] U.S. Cl. .................................... 514/3; 514/4; 530/303; 530/345
[58] Field of Search .................... 530/303, 345; 514/3, 514/4, 866

[56] References Cited

FOREIGN PATENT DOCUMENTS 9007117 6/1990 WIPO .

OTHER PUBLICATIONS

Arslanian et al., "Correlates of Insulin Antibodies in Newly Diagnosed Children with Insulin-dependent Diabetes Before Insulin Therapy", *Diabetes*, vol. 34, pp. 926–930, (1985).

Atkinson et al., "Are Insulin Autoantibodies Markers for Insulin-Dependent Diabetes Mellitus?", *Diabetes*, vol. 35, pp. 894–898, (1986).

Baekkeskov et al., "Identification of the 64K autoantigen in Insulin-dependent diabetes as the GABA-synthesizing enzyme glutamic acid decarboxylase", *Nature*, vol. 347, pp. 151–156, (1990).

Baekkeskov et al., "Autoantibodies in Newly Diagnosed Diabetic Children Immunoprecipitate Human Pancreatic Islet Cell Proteins", *Nature*, vol. 298, pp. 167–169, (1982).

Benson et al., "Insulin Antibodies in Patients Receiving Penicillamine", *The American Journal Of Medicine*, vol. 78, pp. 857–860, (1985).

Berson et al., "Quantitative Aspects of the Reaction Between Insulin and Insulin-Binding Antibody", *The Journal of Clinical Investigation*, vol. 38, pp. 1996–2016, (1959).

Blundell et al., "Insulin: The Structure in the Crystal and its Reflection in Chemistry and Biology", *Advances in Protein Chemistry*, vol. 26, pp. 279–286, (1972).

Bottazzo et al., "Immunology and Diabetes Workshops: Report of the First International Workshop on the Standardization of Cytoplasmic Islet Cell Antibodies", *Diabetologia*, vol. 29, pp. 125–126, (1986).

Bottazzo et al., "Islet-Cell Antibodies in Diabetes Mellitus with Autoimmune Polyendocrine Deficiencies", *The Lancet*, vol. 2, pp. 1279–1283, (1974).

Bromer et al., "Preparation and Characterization of Desoctapeptide-Insulin", *Biochim. Biophys. Acta*, vol. 133, pp. 219–223, (1967).

Bruining et al., "Ten-Year Follow-Up Study of Islet-Cell Antibodies and Childhood Diabetes Mellitus", *The Lancet*, vol. 1, pp. 1100–1103, (1989).

Castano et al., "Identification and Cloning of a Granule Autoantigen (Carboxypeptidase-H) Associated with Type I Diabetes", *J. Clin. Endo. Metab.* vol. 73, No. 6, pp. 1197–1201, (1991).

Cho et al., "Spontaneous Hypoglycemia and Insulin Autoantibodies in a Patient with Graves Disease", *Diabetes Res. Clin. Prac.*, Vol. 3, pp. 119–124, 1987).

Christgau et al., "Pancreatic $\beta$ Cells Express Two Autoantigenic Forms of Glutamic Acid Decarboxylase, a 65-kDa Hydrophilic Form and a 64-kDa Amphiphilic Form Which Can Be Both Membrane-bound and Soluble", *Journal of Biological Chemistry*, vol. 266, No. 31, pp. 21257–21264, (1991).

Darnell et al., "Insulin and Glucagon: Hormonal Regulation of Blood Glucose Levels", *Molecular Cell Biology*, Scientific American Books, Inc. New York, pp. 693–698, (1986).

Dean et al., "Insulin Autoantibodies in the Pre-diabetic Period: Correlation with Islet Cell Antibodies and Development of Diabetes", *Diabetologia*, vol. 29, pp. 339–342, (1986).

Diaz et al., "Differences in Epitope Restriction of Autoantibodies to Native Human Insulin (IAA) and Antibodies to Heterologous Insulin (IA)", *Diabetes*, vol. 36, pp. 66–72, (1987).

Gammeltoft et al., "Insulin Receptors: Binding Kinetics and Structure-Function Relationship of Insulin", *Physiol. Rev.*, vol. 64, pp. 1321–1326, (1984).

Goldman et al., "Characterization of Circulating Insulin and Proinsulin-Binding Antibodies in Autoimmune Hypoglycemia", *The American Society for Clinical Investigation*, vol. 63, pp. 1050–1059, (1979).

Hirata and Ishizu, "Elevated Insulin-Binding Capacity of Serum Proteins in a Case of Spontaneous Hypoglyce- (List continued on next page.)

Primary Examiner—Jill Warden
Assistant Examiner—Benet Prickril
Attorney, Agent, or Firm—Lahive & Cockfield

[57] ABSTRACT

A therapeutic agent that includes a purified peptide bound to a cytotoxic moiety, the peptide being specifically reactive with human insulin autoantibodies and non-reactive with human insulin cell surface receptor, is disclosed.

2 Claims, 4 Drawing Sheets

OTHER PUBLICATIONS mia and Mild Diabetes Not Treated with Insulin", *Tohoku J. Exp. Med.*, vol. 107, pp. 277–286, (1972).

Karjalainen et al., "Relation Between Insulin Antibody and Complement-Fixing Islet Cell Antibody at Clinical Diagnosis of IDDM", *Diabetes*, vol. 35, pp. 620–622, (1986).

Katsoyannis et al., "Studies on the Synthesis of Insulin from Natural and Synthetic A and B Chains; Splitting of Insulin and Isolation of the S-sulfonated Derivatives of the A and B Chains", *Biochemistry*, vol. 6, No. 9, pp. 2635–2642, (1967).

Kurtz et al., "Circulating Insulin-Binding Antibodies", *Diabetologia*, vol. 19, pp. 329–334, (1980).

Larsson et al., "Pancreatic Hormones are Expressed on the Surfaces of Human and Rat Islet Cells Through Exocytotic Sites", *European Journal of Cell Biology*, vol. 48, pp. 45–51, (1989).

Munson and Rodbard, "Ligand: A Versatile Computerized Approach for Characterization of Ligand-binding Systems", *Anal Biochem.*, vol. 107, pp. 220–239, (1980).

Palmer et al., "Insulin Antibodies in Insulin-Dependent Diabetics Before Insulin Treatment", *Science*, vol. 222, pp. 1337–1339, (1983).

Pietropaolo et al., "Molecular Cloning and Characterization of a Novel Neuroendocrine Autoantigen (PM-1) Related to Type I Diabetes", *Diabetes*, vol. 41, supplement 1, Abstr. No. 356, pp. 98A, (1992).

Pullen et al., "Receptor-Binding Region of Insulin", *Nature*, vol. 259, pp. 369–373, (1976).

Rodbard et al., "Quantitative Characterization of Hormone Receptors", *Cancer*, vol. 46, pp. 2907–2918, (1980).

Roep et al., "T-cell reactivity to 38 kD insulin-secretory-granule protein in patients with recent-onset type 1 diabetes", *The Lancet*, vol. 337, pp. 1439–1441, (1991).

Rudinger, "Characteristics of the amino acids as components of a peptide hormone sequence", *Peptide Hormones*, Edited by J. A. Parsons, National Institute for Medical Research, Mill Hill, London University Park Press, pp. 1–7, (1976).

Seino et al., "Characterization of Circulating Insulin in Insulin Autoimmune Syndrome", *Journal of Clinical Endocrinology and Metabolism*, vol. 62, pp. 64–69, (1986).

Sklenar et al., "Spontaneous Hypoglycemia Associated with Autoimmunity Specific to Human Insulin", *Diabetes Care*, vol. 10, pp. 152–159, (1978).

Soeldner et al., "Insulin-Dependent Diabetes Mellitus and Autoimmunity: Islet-Cell Autoantibodies, Insulin Autoantibodies, and Beta-Cell Failure", *New England Journal Of Medicine*, vol. 313, pp. 893–894, (1985).

Srikanta et al., "Autoimmunity to Insulin, Beta Cell Dysfunction, and Development of Insulin-dependent Diabetes Mellitus", *Diabetes*, vol. 35, pp. 139–142, (1986).

Vardi et al., "Prospective Evaluation of Subjects at High Risk for Development of Type I Diabetes Mellitus", *Diabetes*, vol. 36, pp. 1286–1291, (1987).

Vardi et al., "Concentration of Insulin Autoantibodies at Onset of Type I Diabetes Inverse Log-Linear Correlation with Age", *Diabetes Care*, vol. 11, pp. 736–739, (1988).

Wilkin et al., "Value of Insulin Antibodies as Serum Markers for Insulin Dependent Diabetes Mellitus", *The Lancet*, vol. 2, pp. 480–482, (1985).

Yoshimasa et al., "A New Approach to the Detection of Autoantibodies Against Insulin Receptors that Inhibit the Internalization of Insulin into Human Cells", *Diabetes*, vol. 33, pp. 1051–1054, (1984).

Ziegler et al., "Life-Table Analysis of Progression to Diabetes of Anti-Insulin Autoantibody-Positive Relatives of Individuals with Type I Diabetes", *Diabetes*, vol. 38, pp. 1320–1325, (1989).

Steinberger, I. et al. (1991) J. NeuroImmunol. Suppl. 1, p. 59 "Antigen Toxin Chimeric Proteins".

Pastan, I. & Fitz Gerald, D., J. Biol. Chem. 264, 15157–15160 (1989) "Pseudomonas Exotoxin: Chimeric Toxins" All pages.

Olsnes, S. and Pihl, A. (1982) Pharmac. Ther. 15, 355–381 "Chimeric Toxins", All pages.

FitzGerald, D. and Pastan, I. (1989) J. Natl. Cancer. Inst. 81, 1455–1463 "Targeted Toxin Therapy for the Treatment of Cancer", All pages.

Murphy, J. R. (1988) "Immunotoxins" (Frankel, A. E. ed.) Ch. 9, Klower, pp. 123–140 "Diphtheria-related peptide hormane . . . ".

Rudinger, Peptide Hormones (Ed. Parsons) Jun. 1976, pp. 1–7.

Yoshimasa et al., *Diabetes* vol. 33 (Nov. 1984) pp. 1051–1054.

Baekkeskov et al., 1990, *Nature* 347:151–156.

Christgau et al., 1991, *Journal of Biological Chemistry* 266:21257–21264.

Castano et al., 1991, *J. Clin. Endo. Metab.* 73:1197–1201.

Pietropaolo et al., 1992, *Diabetes* 41, supplement 1:98A. (Abstr.).

Roep et al., 1991, *Lancet* 337:1439–1441.

FIG. 1 (PRIOR ART)

INSULIN AUTOANTIBODIES

50% INHIBITORY CONCENTRATION* OF DIFFERENT INSULINS

| PATIENT | ICA | CIAA | HUMAN | PORCINE | BOVINE | RAT | SHEEP | CHICKEN | FISH | GUINEA PIG | PORCINE A-CHAIN | PORCINE B-CHAIN |
|---------|-----|------|-------|---------|--------|------|-------|---------|------|------------|-----------------|-----------------|
| 13.13 | + | 153 | 2.1 | 2.68 | 10.08 | 7.84 | 11.43 | — | >242 | >242 | >242 | >242 |
| 13.15 | + | 183 | 8.06 | 8.06 | 22.4 | — | — | 58.0 | >242 | >242 | >242 | >242 |
| 3.4 | + | 204 | 1.79 | 2.91 | 2.80 | 4.93 | 9.63 | 22.40 | >242 | >242 | >242 | >242 |
| 19.3 | + | 268 | 2.24 | 4.70 | 5.82 | 7.17 | 11.43 | 24.65 | >242 | >242 | >242 | >242 |
| 23.15 | — | 69 | 1.86 | 2.68 | 3.02 | 4.48 | — | — | — | >242 | >242 | >242 |
| 13.1 | — | 99 | 1.12 | 1.79 | 2.68 | 2.68 | 2.99 | 4.03 | >242 | >242 | >242 | >242 |
| 10.8 | — | 218 | 1.95 | 3.58 | 4.03 | 9.63 | 7.6 | 42.5 | >242 | >242 | >242 | >242 |

PREPARATION OF INSULIN ANALOGUE-TOXIN

INSULIN ANALOGUE

↓ Boc-ON

A1,B29-Boc₂ INSULIN ANALOGUE

↓ SPDP

A1,B29-Boc₂ SPDP-INSULIN ANALOGUE

↓ TFA

SPDP-INSULIN ANALOGUE

↓ TOXIN A-CHAIN

INSULIN ANALOGUE-TOXIN CONJUGATE    TOXIN-SS-

*FIG. 5*

PEPTIDES HAVING INSULIN AUTOANTIBODY BUT NOT INSULIN RECEPTOR BINDING CAPACITY

This application is a continuation of U.S. Ser. No. 07/671,455, filed on Mar. 19, 1991, now abandoned.

BACKGROUND OF THE INVENTION

This invention is in the general field of insulin-related peptides.

Human insulin is a two-chain peptide hormone formed in the beta cells of the pancreatic islets of Langerhans. In controlling the level of blood glucose, insulin is the major fuel-regulating hormone in humans and causes a variety of physiological responses. It is believed that a certain portion of the insulin molecule is a receptor-binding region, i.e., that portion of the molecule that binds to receptor molecules on the surface of cells to initiate physiological responses. Gammeltoft, "Insulin Receptors," Physiol. Rev., 64:1321,1322 (1984). More specifically, referring to FIGS. 1 and 2, human insulin consists of an A chain of 21 amino acids SEQ ID NO. 1 and a B chain of 30 amino acids, SEQ ID NO. 2 held in three-dimensional conformation by disulfide bonds. Id. at 1352. The portion of the insulin molecule indicated by the shaded area shown in FIG. 2 is believed to be the receptor-binding region. Id. at 1343.

Diabetes mellitus Type I is a chronic and progressively degenerative illness in which the immune system of the patient produces antibodies which interfere with insulin-related function. In particular, diabetics may produce "auto," or spontaneously occurring, antibodies specific for the beta cells of the pancreatic islets, causing destruction of the cells and thus of the insulin-producing capacity of the patient. Darnell, et al., *Molecular Cell Biology*. Scientific American Books. New York: 1986. In most cases, insulin therapy, consisting of injections of insulin into the patient's bloodstream, can overcome the problem. However, the development of antibodies to insulin in the patient being treated is an accepted consequence of the therapy. Palmer et al., Science, 222:1337 (1983). Human insulin antibodies, or insulin antibodies from other animals arising in an immunological response to insulin injection, are believed to recognize a binding site on the insulin molecule that overlaps the insulin receptor-binding site, for a truncated insulin analogue, desoctapeptide-insulin (B23-30 desoctainsulin), is substantially reduced in both biological and immunologic activity compared to naturally occuring insulin. Bromer et al., Biochim. Biophys. Acta, 133:219 (1967).

Recently, the presence of spontaneously occurring insulin antibodies (or insulin "auto"antibodies) has been reported in the serum of at least 18% of newly diagnosed Type I diabetic patients before they had received any insulin therapy. Palmer et al., Science, 222:1337 (1983). This result has been confirmed by a number of different groups. Arslanian et al., Diabetes, 34:926 (1985); Srikanta et al., Diabetes, 35:139 (1985); Soeldner et al., N.E. J. Med., 313:893 (1985); and Dean et al., Diabetalogia, 29:339 (1986).

SUMMARY OF THE INVENTION

We have discovered that, in contrast with the behavior of insulin antibodies elicited in an immune response to insulin therapy, spontaneously arising human insulin autoantibodies recognize an epitope, or antibody binding site, on the insulin molecule that is distinct from the receptor-binding region of the molecule. Thus, insulin analogues properly designed not to contain the receptor binding site can retain the ability to bind to insulin autoantibodies and yet lack receptor binding (and thus receptor stimulating) ability. Using such insulin analogues, we are able to produce therapeutic agents that can be used safely to inactivate insulin autoantibodies released in the patient's serum and also to target for destruction insulin autoantibody-producing B lymphocytes having insulin autoantibodies exposed on their surface, thereby decreasing the production of insulin antibodies and decreasing T cell responses to insulin.

In one aspect, the invention features a therapeutic agent including a purified peptide bound to a cytotoxic moiety, the peptide being specifically reactive with human insulin autoantibodies and non-reactive with human insulin cell surface receptor. By "specifically reactive with" insulin autoantibodies is meant that the peptide is capable of specifically recognizing human insulin autoantibodies in preference to other antibodies and that the immunologic reactivity or binding between the peptide and human insulin autoantibody is at least 50% of the level of reactivity of insulin with human insulin autoantibodies. By "non-reactive with human insulin cell surface receptor" is meant that the peptide has less than 1% of the receptor binding activity of insulin. Therefore, the peptide is unable to initate the physiological responses of the cell to insulin.

Preferred embodiments include the following features. The cytotoxic moiety is a toxic portion of a toxin molecule; the peptide is an analogue of human insulin including an A chain and a B chain; the A chain includes, at positions A12 and A13, the amino acid residues at positions A12 and A13 of human insulin, or conservative substitutions thereof; the B chain includes, at position B3 of human insulin, the amino acid residue at position B3 of human insulin, or a conservative substitution thereof; and the B chain has a C-terminus before amino acid residue B23 of human insulin. Alternatively, the A chain of the human insulin analogue includes the above-indicated amino acid residues at positions A12, A13, and B3, and the A and B chains further include at least one non-conservative substitution for an amino acid at any one of positions A1, A21, B12, B16, B24, B25, or B26 of the corresponding A chain or the B chain of human insulin. By "analogue" of human insulin is meant a peptide whose general tertiary structure resembles that of insulin but whose amino acid sequence has been modified. By "conservative substitution" is meant a substitution for the indicated amino acid that does not substantially affect the antibody binding function of the peptide. By "non-conservative substitution" is meant a substitution for the indicated amino acid that does substantially affect the antibody binding function of the peptide. Analogues of insulin included within the claims have the property of being specifically reactive with human insulin autoantibodies and non-reactive with human insulin cell surface receptor as defined. When the above description is applied to analogues in which amino acids at specific positions in the insulin A and B chains have been deleted from the corresponding positions in the analogue, the analogue still retains the numbering system that would permit the greatest correspondence with the numbering system of the A and B chains of insulin.

In particularly preferred embodiments, the peptide is desoctapeptide(B23-B30)-insulin or an analogue of human insulin in which the A chain includes the amino acid residues at positions A11–A14 of human insulin and the B chain includes the residues at positions B1–B4 of human insulin.

In other aspects, the invention features a method for controlling human insulin autoimmunity in a patient and a method for gradually inducing patient tolerance to insulin. The methods include the steps of providing a therapeutic agent that includes a purified peptide specifically reactive with human insulin autoantibodies and non-reactive with human insulin cell surface receptor, and administering to the patient a therapeutically effective amount of the agent in a pharmaceutically acceptable carrier substance. In preferred embodiments of the method for controlling human insulin autoimmunity, the peptide is bound to a cytoxic moiety, preferably the toxic portion of a toxin molecule which, most preferably, is ricin or diphtheria toxin. In preferred embodiments of either method, the therapeutic agent includes the preferred peptide described above.

In yet another aspect, the invention features a method for detecting the presence of human insulin autoantibodies in a patient. The method includes the steps of providing a sample of serum from a patient, contacting the serum with a purified peptide that is specifically reactive with human insulin autoantibodies and non-reactive with human insulin cell surface receptor, and measuring the amount of binding of the peptide to the serum sample. In a similar method, the presence of human insulin-related autoantibodies in a patient can be detected by contacting a sample of serum from the patient with purified human proinsulin or with a purified peptide analogue of proinsulin that includes an A chain, comprising the amino acid residues at positions A12 and A13 of human proinsulin or conservative substitutions thereof, and a B chain, comprising the amino acid residue at position B3 of human proinsulin or a conservative substitution thereof.

The invention provides for agents and methods of using them that will diagnose and destructively target insulin autoantibodies in serum, or the autoantibody-producing B lymphocytes, and thus help prevent the onset of Type I diabetes mellitus without triggering the physiological responses that are a consequence of insulin/receptor binding. Because insulin has been so thoroughly studied, the agents are easy to make by standard molecular or biochemical techniques.

Other features and advantages of the invention will be apparent from the following description of the preferred embodiment thereof and from the claims.

BRIEF DESCRIPTION OF THE DRAWINGS

FIG. 1 is a representation of the amino acid sequence of the A and B chains of human insulin and the differences in sequence in a number of insulins from other species and in selected insulin analogues.

FIG. 3 is a table showing the concentration of various insulins required for 50% inhibition of $^{125}$I-insulin binding for a given serum.

FIG. 5 is a representation of the sequence of steps for the preparation of an insulin analogue/toxin conjugate.

DESCRIPTION OF THE PREFERRED EMBODIMENTS

The invention features peptide analogues of insulin which retain the ability of the insulin molecule to be immunologically reactive with insulin autoantibodies present in the serum of patients having pre Type I diabetes mellitus, while at the same time the peptides are biologically non-reactive with insulin receptor. Preferred analogues contain the epitope to which human anti-insulin autoantibodies bind and lack the insulin receptor binding portion of the insulin molecule.

Such analogues can be used therapeutically, e.g., as a carrier for a toxin molecule to target insulin autoantibodies or insulin autoantibody-producing B lymphocytes, thus reducing the concentration of insulin autoantibodies, or decreasing their production, without triggering a diabetic's characteristic response to insulin stimulation.

1. Determination of an epitope recognized by human anti-insulin autoantibodies that is distinct from the insulin receptor binding domain.

Insulin autoantibodies isolated from sera of well-characterized first-degree relatives of patients with Type I diabetes mellitus were analyzed in comparative studies by competition with a series of insulins from different species and with insulin analogues. Insulin binding activity was detected using a competitive binding radioassay and expressed in nU of insulin precipitated per ml of sera (1 nU/ml=7.18 fmole/L). Each of the studied individuals consistently had insulin autoantibodies for at least one year. The data indicate that these Type I diabetes-associated autoantibodies are homogeneous.

Figure 4:
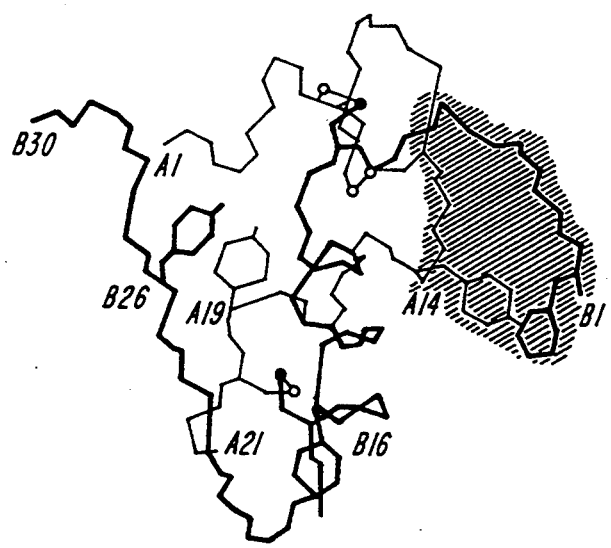
FIG. 4 is a representation of the three-dimensional structure of insulin, showing the human insulin autantibody-binding site.

Using the results of the comparative studies, a recognition epitope for human anti-insulin autoantibodies arising in Type I diabetes was mapped and shown to include regions A11–A14 and B1–B4 of the insulin molecule and not to include regions A17 and B23–B30. Referring to FIG. 4, the included regions can be seen to be adjacent to one another in insulin's three dimensional crystallographic structure. At the same time, referring to FIG. 2, the autoantibody-binding region of the insulin molecule can be distinguished from the insulin receptor-binding domain that lies on the opposite surface of the molecule; specific details are given below.

Figure 1:
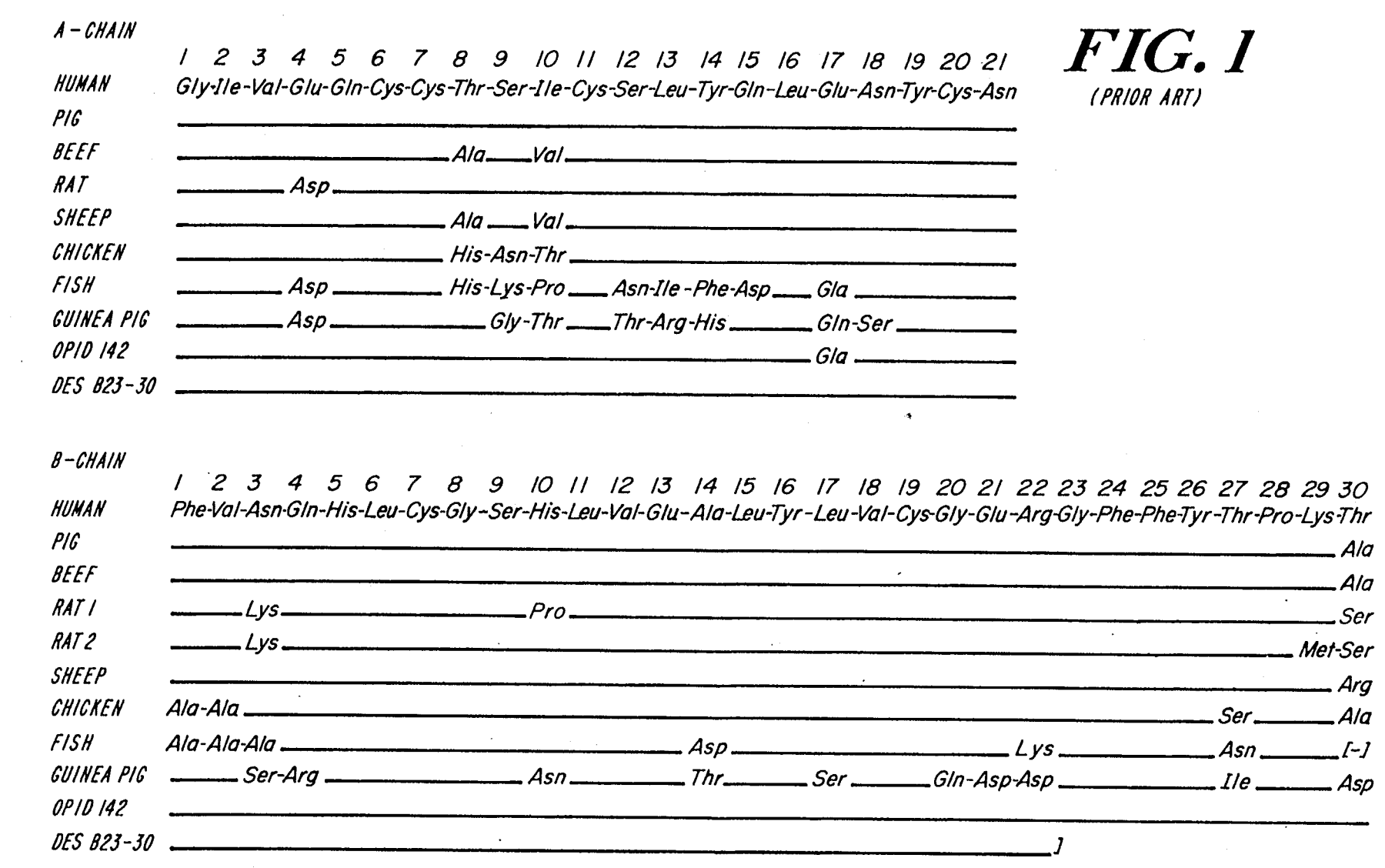

Competition of a series of insulins and insulin analogues, whose amino acid sequences are given in FIG. 1, with $^{125}$I-human insulin for binding to human insulin autoantibodies isolated from patient sera was evaluated. Referring to FIG. 3, human insulin consistently inhibited binding at lower concentrations than the other insulins, and the rank order potency of various insulins was similar for different sera. Guinea pig insulin failed to compete in concentrations 1000 times greater than that which gave maximal inhibition with human insulin. Fish (salmon) insulin also competed poorly. All other species of insulin studied gave similar maximal inhibition of $^{125}$I-human insulin precipitation. Two specific insulin analogues were studied: GluA17→Gln human insulin (similar to fish (salmon) and guinea pig insulin) and desoctapeptide(B23–B30)-insulin, an analogue lacking the carboxyl terminal eight amino acids of the B chain. Both of these analogues competed effectively for $^{125}$I-insulin binding to insulin autoantibodies.

In human proinsulin the N-terminus of the insulin A-chain (GlyA1) is connected to the C-terminus of the B-chain (ThrB30) by a 35 amino acid connecting peptide. In contrast to all other insulin analogues studied, human proinsulin was found to be at least as potent as human insulin in binding to insulin autoantibodies, and for several patients only proinsulin autoantibodies were found.

Although the affinities and capacities of the autoantibodies from different subjects varied, for all subjects the overall order of immunologic recognition of the insulins and related analogues was similar. Comparisons between the sequences of these insulins allows an autoantibody recognition domain to be mapped.

The primary sequence of porcine insulin differs from human insulin by one residue; bovine, rat and ovine insulins each differs from human by three amino acids (FIG. 1). Each of these insulins exhibits high-affinity recognition by the human insulin autoantibodies. The affinity of chicken insulin, which differs from human insulin at 7 positions, is reduced ∼20-fold. The affinity of the human insulin autoantibodies for fish insulin is markedly reduced, and guinea pig insulin is essentially not recognized by the insulin autoantibodies. These insulins differ from human insulin at 15 and 18 different positions, respectively.

In bovine and ovine insulins, residues ThrA8 and IleA10 of human insulin are substituted by alanine and valine, respectively; these conservative changes result in a minimal reduction in insulin autoantibody binding affinity. In contrast, the A8–A10 positions of chicken and salmon insulin and A9–A10 positions of guinea pig insulin, all insulins with reduced insulin autoantibody affinity, are substituted non-conservatively. More significant regions of sequence dissimilarity can be mapped to A13–A15, A17, B1–B3 and B27 domains of insulin. Analogues GluA17→Gln insulin and desoctapeptide(B-23–B30)-insulin compete for binding effectively, demonstrating that the A17 and B27 positions are not important for human insulin autoantibody recognition.

Insulin autoantibodies from several patients with the autoimmune syndrome differ dramatically from the Type I diabetes associated insulin autoantibodies studied here. In particular, such patients have been reported to have markedly higher insulin binding capacities, and for several patients the epitope of insulin recognized by the autoantibodies can distinguish porcine from human insulin. Porcine insulin differs from human insulin only at the B30 residue (threonine changed to alanine), a residue unimportant for reactivity of Type I diabetes-associated insulin autoantibodies.

From these comparative studies we have mapped the recognition epitope for human anti-insulin autoantibodies arising in Type I diabetes mellitus to include regions A11–A14 and B1–B4. Referring to FIG. 4, these regions can be seen to be adjacent to one another in insulin's three dimensional crystallographic structure.

Figure 2:
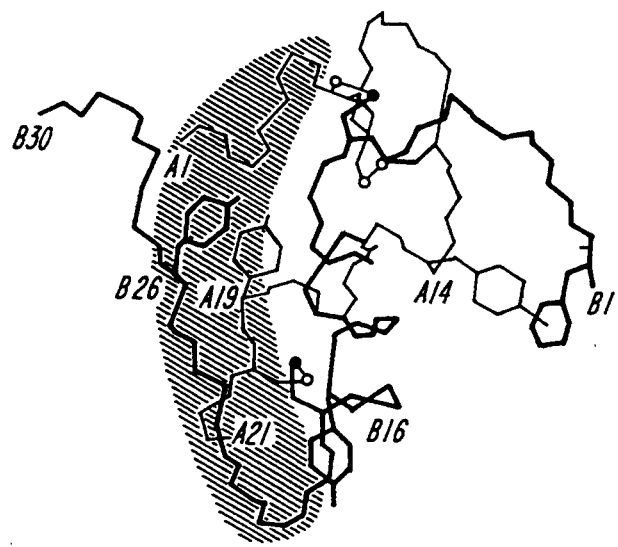
FIG. 2 is a representation of the three-dimensional structure of insulin, showing the insulin receptor-binding site.

The receptor binding region of insulin, as indicated in FIG. 2, has been mapped previously by comparing primary sequences and biologic potencies of insulins from many species and related analogues to the crystallographic structure of insulin. Gammeltoft, supra, p. 1349. Residues at the amino-(GlyA1, GlnA5) and carboxyl-terminus (TyrA19, AsnA21) of the A-chain and the center (VB12, TyrB16) and carboxyl-terminus (PheB24, PheB25, TyrB26) of the B-chain are thought to be involved directly in receptor recognition. This is in striking contrast to the residues contributing to the dominant immunogenic epitope of this study. The epitope of insulin that reacts with the insulin autoantibodies can therefore be distinguished from insulin's receptor binding domain which lies on the opposite surface of the three-dimensional structure of the insulin molecule.

2. Preparation of insulin analogues that are immunologically active but inactive metabolically Given the information obtained concerning the separation of the insulin autoantibody and insulin receptor binding activity, specific analogues can be prepared that are presumed to retain autoantibody binding activity while at the same time to lack receptor binding activity. Some appropriate analogues are desoctapeptide(B-23–B30)-insulin or proinsulin; desheptapeptide(B-24–B30)-insulin or proinsulin; despentapeptide(A1–A5)-insulin or proinsulin; des-(A21) proinsulin; insulin or proinsulin modified at GlyA1, ValB12, TyrB16, PheB24, or PheB25 with a non-conservative substitution (e.g., Arg or Glu) or chemically; or combinations of the above.

The analogues can then be screened in the following manner:

Human autoantibody binding affinity is determined by reacting autoantibodies obtained from new onset Type I diabetics prior to insulin therapy (sera from such patients is readily available worldwide) with the appropriate analogue and then determining competition with $I^{125}$ insulin by Scatchard analysis. Receptor binding activity is also determined by Scatchard analysis utilizing a series of standard insulin receptor assays including reactivity with whole cells and with purified normal human receptors. In addition, bioactivity can be determined by injecting an analogue-containing solution intravenously or subcutaneously into humans or animals and then monitoring blood glucose levels. In humans, a standard insulin tolerance test involves intravenously injecting 0.1 U/kg insulin and then monitoring blood glucose levels over a ½ hour period. In a more formal procedure, a euglycemic glucose clamp can be employed, with the intravenous infusion of insulin, or the analogue being tested, and glucose; the end point is glucose utilization. Acceptable analogues should have greater than 50% of the affinity of human insulin for pre-diabetic insulin autoantibodies and less than 1% of the bioactivity of human insulin.

3. Preparation of therapeutic agents

Referring to FIG. 5, an insulin analogue/toxin conjugate is prepared according to the following scheme: An appropriate insulin analogue, selected as described above, is reversibly modified with the t-butyloxycarbonyl (Boc) group selectively at $A1^\alpha$ and $B29^\epsilon$ positions; the $B1^\alpha$ amino group is not modified. This material is then reacted with N-succinimidyl 3-(2-pyridyldithio) propionate (SPDP) to form SPDP-insulin. Following removal of boc groups $B1^\alpha$-SPDP-insulin is obtained in pure form. This is reacted with the free sulfhydryl group of Toxin A chain (e.g., of a peptide toxin such as ricin, diphtheria toxin, etc.) to form a disulfide-linked conjugate.

Use

Insulin analogues that dissociate receptor from immunogenic binding can be used in broad based therapy for the detection of incipient Type I diabetes mellitus and the prevention of further development of the condition.

For detection of insulin autoimmunity heralding Type I diabetes, analogues having specifically designed epitopes, so as to react with a subset of human insulin autoantibodies, can be prepared.

Proinsulin is an excellent agent for detecting insulin autoimmunity. As described earlier, human proinsulin is at least as potent as human insulin in binding to insulin autoantibodies, and in some patients only proinsulin autoantibodies are found at early stages of diabetes development.

Radioactive biotinylated or otherwise labeled proinsulin, or insulin or proinsulin analogue, can be utilized in a fluid phase assay as a diagnostic reagent to detect pre Type I autoimmunity. The reagent, with invarient residues A12, A13, B1, B2 and B3, should be labeled at sites distinct from those residues (e.g., at TyrA14 or at TyrB26). Specifically, a kit for detecting pre Type I diabetes mellitus can be prepared for routine use in a hospital setting. Such a kit would include a container to receive a sample of serum from a patient; a measured amount of purified, labeled human proinsulin (or insulin or proinsulin analogue) to be placed in contact with the serum sample; and a filter or standard means of precipitation (e.g., 14% polyethylene glycol) for recovering the antibody population in the serum so as to permit measurement of the amount of specific binding of the labeled reagent to the serum sample.

In a therapeutic context, analogues of insulin with minimal receptor binding activity but greater than 50% immunogenic activity can be administered intravenously or orally in doses of 0.01 mg to 10 mg/kg/day to induce patient tolerance to insulin.

For a more immediate effect, an appropriate analogue can be coupled to, e.g., diphtheria toxin, as described above, and administered intravenously or subcutaneously (in doses of 0.01 mg to 10 mg/kg/day). Such a toxin conjugate can specifically target autoreactive B lymphocytes thereby decreasing the production of insulin autoantibodies, and can eliminate the insulin specific B lymphocyte presentation to T cells of insulin or proinsulin, thus reducing T cell responses to insulin.

---

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
    ( A ) LENGTH: 21
    ( B ) TYPE: amino acid
    ( C ) STRANDEDNESS: Not Relevant
    ( D ) TOPOLOGY: linear ( x i ) SEQUENCE DESCRIPTION: SEQ ID NO: 1:

Gly Ile Val Glu Gln Cys Cys Thr Ser Ile Cys Ser Leu Tyr Gln Leu
                    5                   10                  15
Glu Asn Tyr Cys Asn
            20

( 2 ) INFORMATION FOR SEQ ID NO: 2:

( i ) SEQUENCE CHARACTERISTICS:
    ( A ) LENGTH: 30
    ( B ) TYPE: amino acid
    ( C ) STRANDEDNESS: Not Relevant
    ( D ) TOPOLOGY: linear ( x i ) SEQUENCE DESCRIPTION: SEQ ID NO: 2:

Phe Val Asn Gln His Leu Cys Gly Ser His Leu Val Glu Ala Leu Tyr
                    5                   10                  15
Leu Val Cys Gly Glu Arg Gly Phe Phe Tyr Thr Pro Lys Thr
            20                  25                  30

---

Other embodiments are in the claims.

What is claimed is:

1. A therapeutic compound comprising a purified peptide bound to a cytotoxic peptide moiety capable of decreasing the production of insulin autoantibodies by B lymphocytes, said peptide being specifically reactive with human insulin autoantibodies and biologically non-reactive with human insulin cell surface receptor, wherein said peptide comprises an A chain of human insulin and a B chain of human insulin, and wherein said B chain is desoctapeptide (B23–B30)-insulin.

2. The compound of claim 1, wherein said cytotoxic peptide moiety comprises the toxic portion of a toxin molecule chosen from ricin or diptheria toxin.

* * * * *

UNITED STATES PATENT AND TRADEMARK OFFICE
CERTIFICATE OF CORRECTION

PATENT NO. : 5,422,339
DATED : June 6, 1995
INVENTOR(S) : George S. Eisenbarth et al.

It is certified that error appears in the above-identified patent and that said Letters Patent is hereby corrected as shown below:

<u>Column 1,</u>
Before BACKGROUND OF INVENTION, insert the following paragraph:

-- STATEMENT REGARDING FEDERALLY SPONSORED RESEARCH
This invention was made with support from the U.S. government under grant number DK 32083 awarded by the National Institutes of Health. The government has certain rights in the invention. --.

Signed and Sealed this

Fourth Day of March, 2003

JAMES E. ROGAN
*Director of the United States Patent and Trademark Office*